(12) United States Patent
Dahl et al.

(10) Patent No.: US 10,111,644 B2
(45) Date of Patent: Oct. 30, 2018

(54) METHOD OF COHERENT FLOW IMAGING USING SYNTHETIC TRANSMIT FOCUSING AND ACOUSTIC RECIPROCITY

(71) Applicant: The Board of Trustees of the Leland Stanford Junior University, Palo Alto, CA (US)

(72) Inventors: Jeremy Joseph Dahl, Palo Alto, CA (US); You Leo Li, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 102 days.

(21) Appl. No.: 15/479,002

(22) Filed: Apr. 4, 2017

(65) Prior Publication Data

US 2017/0281121 A1 Oct. 5, 2017

Related U.S. Application Data

(60) Provisional application No. 62/318,614, filed on Apr. 5, 2016.

(51) Int. Cl.

| | |
|---|---|
| *G01N 29/02* | (2006.01) |
| *G01N 29/22* | (2006.01) |
| *G01N 29/44* | (2006.01) |
| *G01N 29/52* | (2006.01) |
| *A61B 8/08* | (2006.01) |
| *A61B 8/14* | (2006.01) |
| *A61B 8/06* | (2006.01) |
| *G01S 7/52* | (2006.01) |

(52) U.S. Cl.
CPC ............. *A61B 8/06* (2013.01); *A61B 8/145* (2013.01); *A61B 8/5223* (2013.01); *G01N 29/02* (2013.01); *G01N 29/221* (2013.01); *G01N 29/222* (2013.01); *G01N 29/44* (2013.01); *G01S 7/52036* (2013.01); *A61B 8/5207* (2013.01); *G01N 2291/02466* (2013.01); *G01N 2291/02836* (2013.01); *G01N 2291/106* (2013.01)

(58) Field of Classification Search
CPC .. G01S 7/52036; G01N 29/221; G01N 29/222; G01N 29/02; G01N 29/44; G01N 2291/02466; G01N 2291/02836; G01N 2291/106; A61B 8/06; A61B 8/5223; A61B 8/145; A61B 8/5207
USPC .......................................................... 73/606
See application file for complete search history.

(56) References Cited

U.S. PATENT DOCUMENTS

| | | | | |
|---|---|---|---|---|
| 4,694,434 A | * | 9/1987 | von Ramm | G01S 7/52068 345/419 |
| 6,216,540 B1 | * | 4/2001 | Nelson | A61B 5/0091 73/633 |

(Continued)

*Primary Examiner* — J M Saint Surin
(74) *Attorney, Agent, or Firm* — Lumen Patent Firm

(57) ABSTRACT

Acoustic imaging based on angular coherence is provided. The target is insonified with collimated acoustic beams at several different incidence angles. The resulting images are processed to determine angular coherence averaged over angle, and then integration of the angular coherence for relatively small angular differences is used to provide the output angular coherence image. In cases where flow imaging is done, the images are first filtered to suppress signals from stationary features of the target, multiple acquisitions are acquired, and the final flow image is computed by summing the squares of the angular coherence images (on a pixel by pixel basis).

12 Claims, 9 Drawing Sheets

(56) References Cited

U.S. PATENT DOCUMENTS

| | | | |
|---|---|---|---|
| 6,552,841 B1 * | 4/2003 | Lasser | G01N 29/0609 |
| | | | 359/305 |
| 2009/0306510 A1 * | 12/2009 | Hashiba | G01S 15/8925 |
| | | | 600/447 |
| 2011/0030448 A1 * | 2/2011 | Moore | G01N 29/30 |
| | | | 73/1.82 |
| 2013/0109971 A1 | 5/2013 | Dahl et al. | |
| 2015/0293222 A1 * | 10/2015 | Huang | G01S 15/8977 |
| | | | 367/7 |
| 2015/0342567 A1 | 12/2015 | Ustuner et al. | |

\* cited by examiner

METHOD OF COHERENT FLOW IMAGING USING SYNTHETIC TRANSMIT FOCUSING AND ACOUSTIC RECIPROCITY

CROSS REFERENCE TO RELATED APPLICATIONS

This application claims the benefit of U.S. provisional patent application 62/318,614, filed on Apr. 5, 2016, and hereby incorporated by reference in its entirety.

GOVERNMENT SPONSORSHIP

This invention was made with Government support under contracts EB015506 and HD086252 awarded by the National Institutes of Health. The Government has certain rights in the invention.

FIELD OF THE INVENTION

This invention relates to acoustic imaging.

BACKGROUND

Improving signal vs. noise in acoustic imaging is of general interest for various applications, including medical imaging. One approach that has been considered for accomplishing this is use of coherence imaging, which is based on the typically different coherence exhibited by acoustic signals from a target and electronic noise. However, conventional coherence-based techniques such as short-lag spatial coherence (SLSC) and coherent flow power Doppler (CFPD) undesirably provide non-uniform resolution. Accordingly, it would be an advance in the art to provide improved coherence-based acoustic imaging.

SUMMARY

In this work, we provide acoustic imaging based on angular coherence (as opposed to spatial coherence). The target is insonified with collimated acoustic beams at several different incidence angles. The resulting images are processed to determine angular coherence by averaging over angle, and then integration of the angular coherence for relatively small angular differences is used to provide the output angular coherence image. In cases where flow imaging is done, multiple acquisitions are acquired, the images are first filtered to suppress signals from stationary features of the target, and the final flow image is computed by summing the squares of the angular coherence images (on a pixel by pixel basis).

Significant advantages are provided. Fast acquisition, uniform image resolution, and low noise are simultaneously provided. More specifically:
1. Compared to conventional short-lag spatial coherence (SLSC) and coherent flow power Doppler (CFPD) flow imaging methods (which utilize spatial coherence beamforming), this work provides uniformly high image resolution with noise reduction. Conventional SLSC and CFPD have a non-uniform resolution, which deteriorates with distance from the focus; this work provides uniformly high resolution over the entire image.
2. Compared to synthetic transmit focusing techniques utilized with conventional B-mode and flow imaging techniques, this work provides better suppression of electronic noise, and thus better image quality deep in tissue.
3. Compared to conventional synthetic-transmit-focusing with short-lag spatial coherence beamforming, this work provides higher power output and significantly reduces the acquisition and image reconstruction time.

This work is suitable for use with any application of acoustic imaging, including but not limited to medical imaging and non-destructive evaluation of industrial parts. It is expected to be especially useful in connection with ultrasound flow imaging of slow flow and small blood vessels or the vasculature deep in tissue of the difficult-to-image patient (e.g. overweight/obese patients).

DETAILED DESCRIPTION

Figure 1:
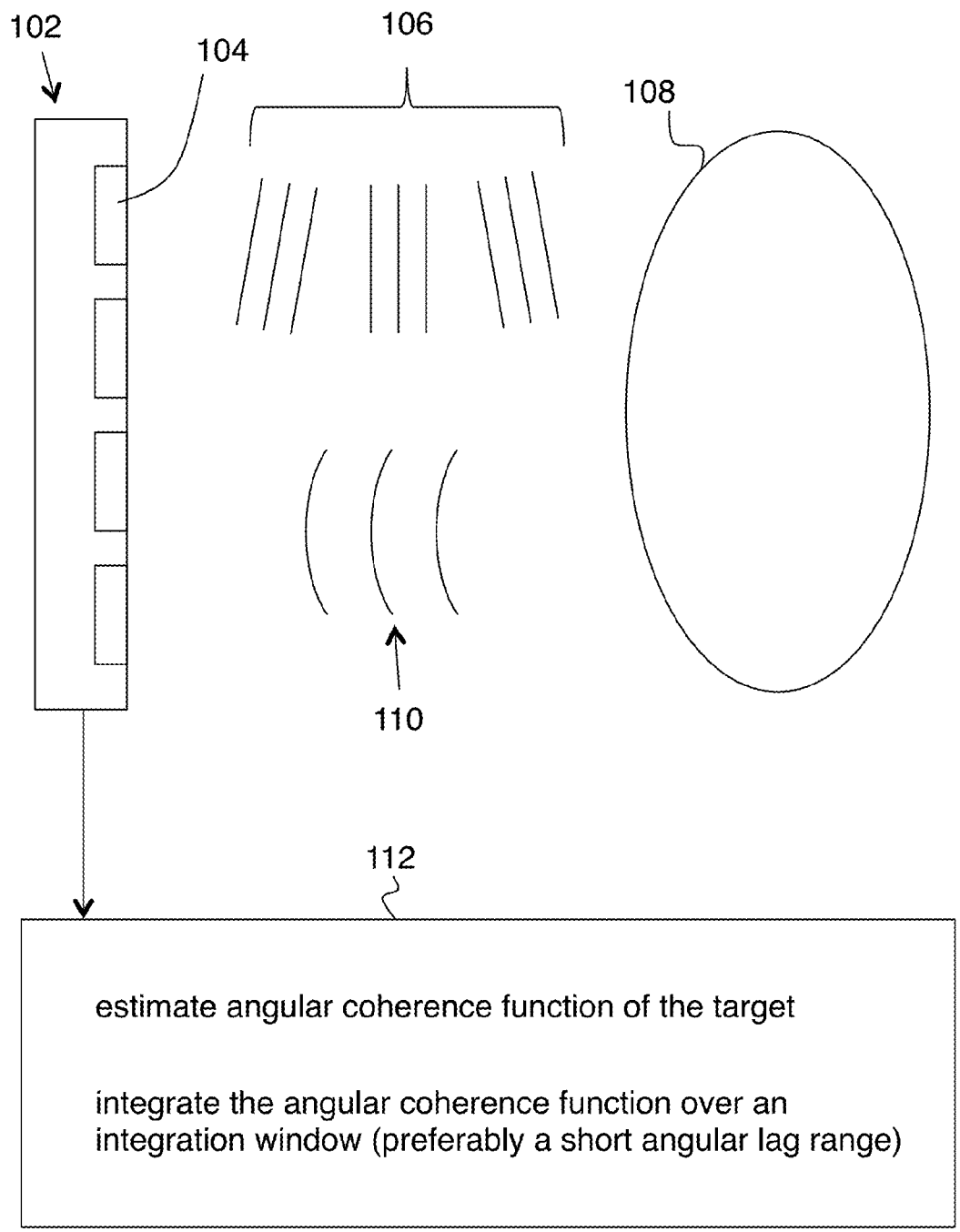
FIG. 1 shows an embodiment of the invention.

FIG. 1 shows operation of an exemplary embodiment of the invention. An acoustic imaging system includes an acoustic transducer array 102 and a processor 112. Here this array is shown as having four elements 104, but any number of elements can be included in the transducer array, and the transducer array can be one-dimensional or two-dimensional. Collimated acoustic radiation 106 is emitted from the acoustic transducer array at a target 108 at three or more distinct incidence angles (as schematically shown on FIG. 1). Scattered acoustic radiation 110 from the target is received with the acoustic transducer array 102. Acoustic images of the target from the scattered acoustic radiation are determined corresponding to each of the three or more incidence angles. An angular coherence image is computed with the processor 112 by at least:
i) averaging the acoustic images vs. angle to estimate an angular coherence function at each spatial point of the acoustic images; and
ii) integrating the angular coherence function over a predetermined angular range to provide the angular coherence image. This angular coherence image can be provided as an output.

Here a collimated acoustic beam is an acoustic beam with substantially planar wavefronts in all locations within the field-of-view. The half divergence angle of such a beam in homogeneous media is smaller than or equal to three times the limit imposed by the diffraction of the acoustic aperture that is used to generate the beam. For a Gaussian beam with half width w and wavelength $\lambda$, the intended half divergence angle $\theta$ is roughly $\theta \leq 3\lambda/(\pi w)$. With inhomogeneous media, aberration may increase the half divergence angle.

The predetermined angular range is preferably less than or equal to 30% of a total angular range of the three or more distinct incidence angles.

The acoustic images can be provided as complex-valued functions of two spatial variables or as real-valued functions of two spatial variables. Complex-valued functions can be represented as having real and imaginary components in the averaging the acoustic images vs. angle. Alternatively, complex-valued functions can be represented as having in-phase and quadrature components in the averaging the acoustic images vs. angle. Real-valued functions can represent radio-frequency ultrasound signal intensity in the averaging the acoustic images vs. angle. Radio-frequency signals in the context of ultrasound imaging are the ultrasound echoes recorded by the transducers as a function of time or depth.

Averaging the acoustic images vs. angle can further include spatial averaging over a predetermined spatial range. For example, if the acoustic imaging system provides an axial resolution the spatial averaging can be done over an axial range substantially equal to the axial resolution. Similarly, if the acoustic imaging system provides a lateral resolution the spatial averaging can be done over a lateral range substantially equal to the lateral resolution. As used herein, "substantially equal" means equal to within +/−10%.

The three or more distinct incidence angles are preferably seven or more distinct incidence angles. The acoustic images can be 2-D brightness mode images. Alternatively, the acoustic images can be flow acoustic images that are filtered to suppress signals from stationary parts of the target. In such cases, it is preferred to perform angular coherence imaging for three or more acquisitions that are separated by a predetermined time delay, and to provide an output flow image by summing squares of the angular coherence image for each acquisition.

More specifically, flow imaging according to the present approach can be accomplished as follows 1) Plane waves with different transmit angles are emitted, each of which produces one acoustic image. The acoustic images produced in this step are denoted as (Angle 1, Acquisition 1), (Angle 2, Acquisition 1), (Angle 3, Acquisition 1), and etc.
2) Wait for a fixed amount of time (e.g., 1 ms).
3) Repeat step 1 and 2 for at least two more times (at least 3 times in total). The images produced in this step are denoted as (Angle 1, Acquisition 2), (Angle 2, Acquisition 2), (Angle 3, Acquisition 2), and (Angle 1, Acquisition 3), (Angle 2, Acquisition 3), (Angle 3, Acquisition 3), and etc.
4) Filter the acoustic images to remove stationary signals. The filtering is conducted among images produced with the same angle index but different acquisition indices. For example, Angle 1 images in all acquisitions, including (Angle 1, Acquisition 1), (Angle 1, Acquisition 2), (Angle 1, Acquisition 3), and so on, are filtered as one ensemble; and then Angle 2 images in all acquisitions; and so on. The result is one filtered flow image corresponding to each of the acquired acoustic images.
5) Produce one angular coherence image from the filtered images in Acquisition 1, including (Angle 1, Acquisition 1), (Angle 2, Acquisition 1), (Angle 3, Acquisition 1), and so on as described above. Then similarly produce one angular coherence image for each of the other acquisitions.
6) Sum the squares of the angular coherence images.

FIGS. 2A-D schematically show incident and scattered acoustic radiation. Here 202 is a point in the sample being imaged, 204 is an incident plane wave at a first incidence angle, and 206 is the corresponding backscattered acoustic radiation. The backscattered wave is detected by the acoustic transducer array and converted to electrical signals. 208 is an incident plane wave at a second incidence angle, and 210 is the corresponding scattered acoustic radiation. The backscattered wave is detected by the acoustic transducer array and converted to electrical signals.

Figure 3A:
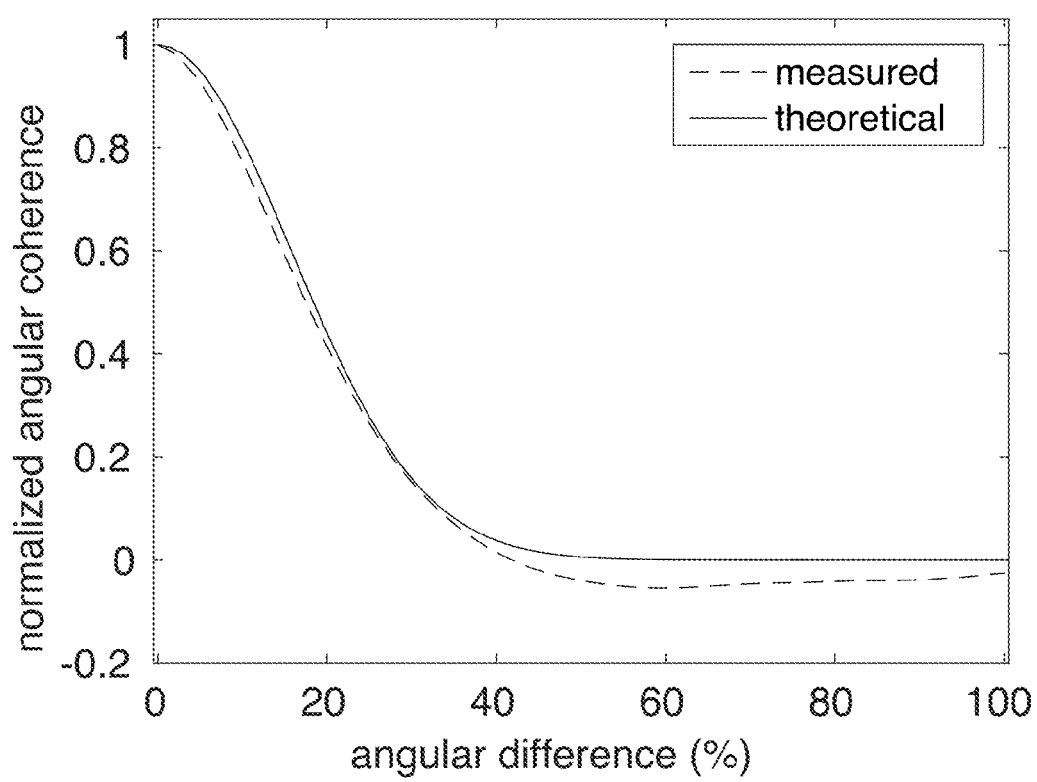
FIGS. 3A-C show simulated and theoretical angular coherence functions for three different apodization functions.
Figure 3B:
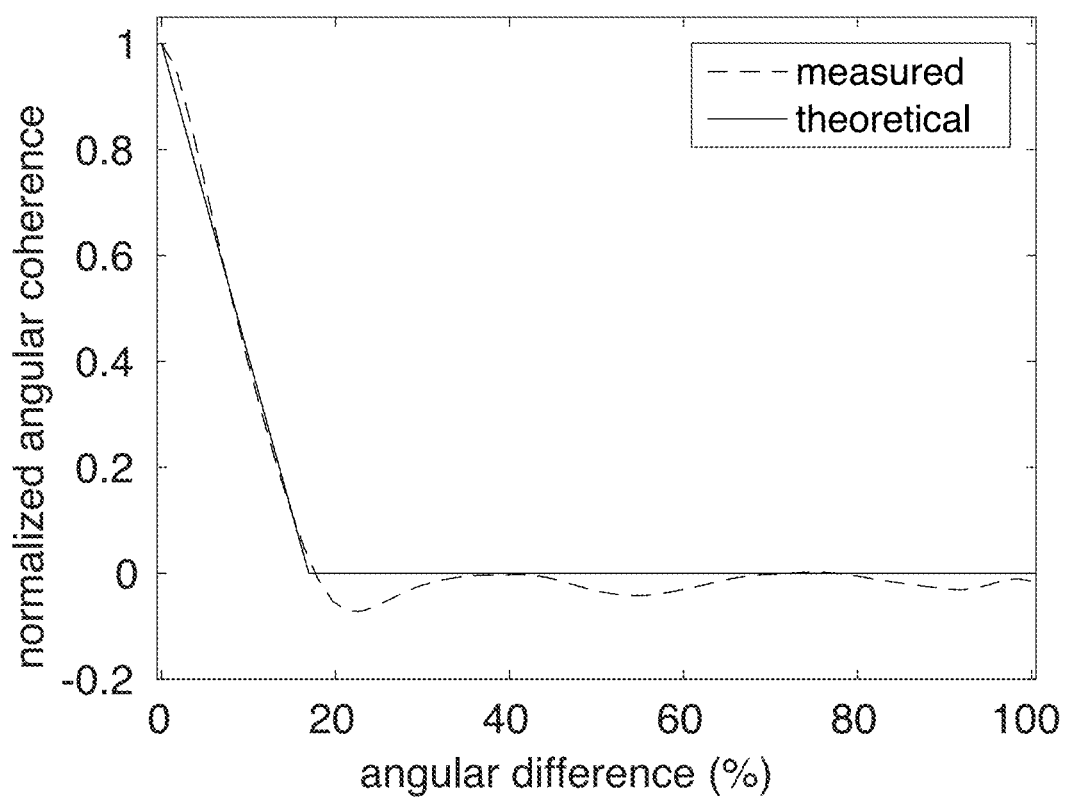
Figure 3C:
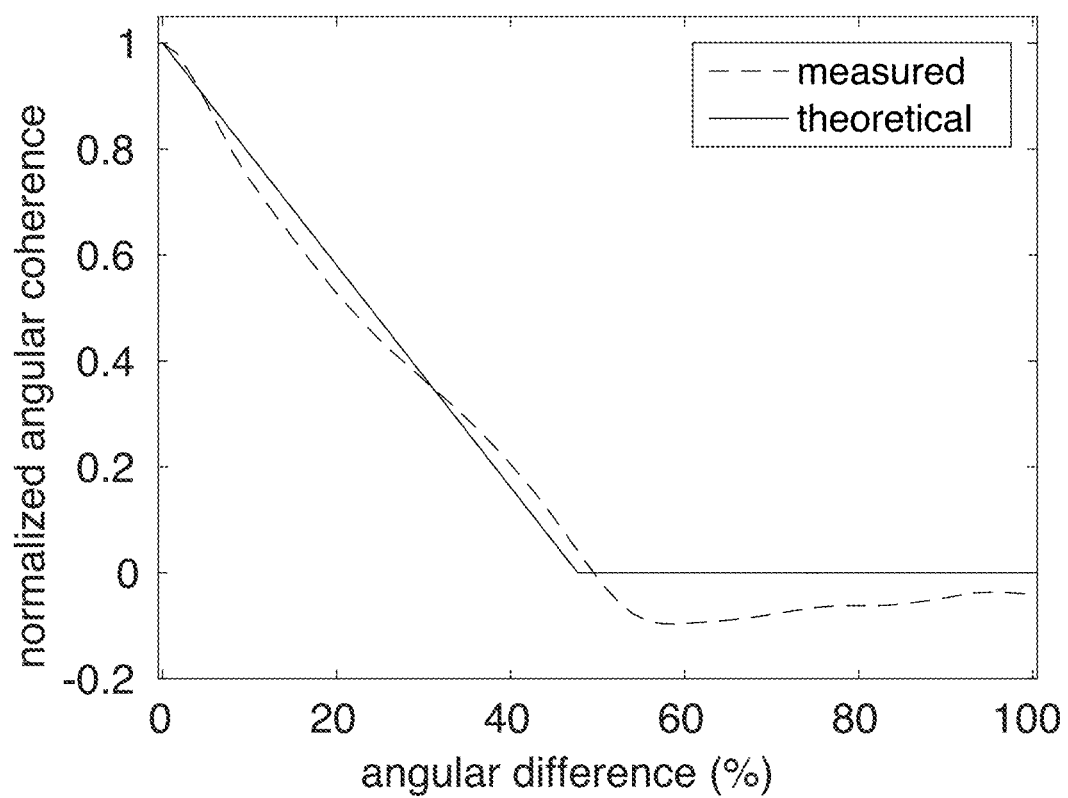

FIGS. 3A-C show angular coherence as functions of angular spacing between plane wave transmits measured from simulations. The angular spacing is expressed as a fraction of the receive angular range (28° in this case). The solid curves represent theoretical predictions, and the dashed curves represent measurement average and standard deviation from 5 simulations with independent speckle realizations. Three types of receive apodization functions were used: (FIG. 3A) Gaussian apodization with a standard deviation of 7.81% of the receive aperture size; (FIG. 3B) rectangular apodization with a window width of 7.81% of the receive aperture size; and (FIG. 3C) rectangular apodization with a window width of 23.44% of the receive aperture size. For all three cases, the theoretical predictions closely match the measured coherence curves.

Figure 4:
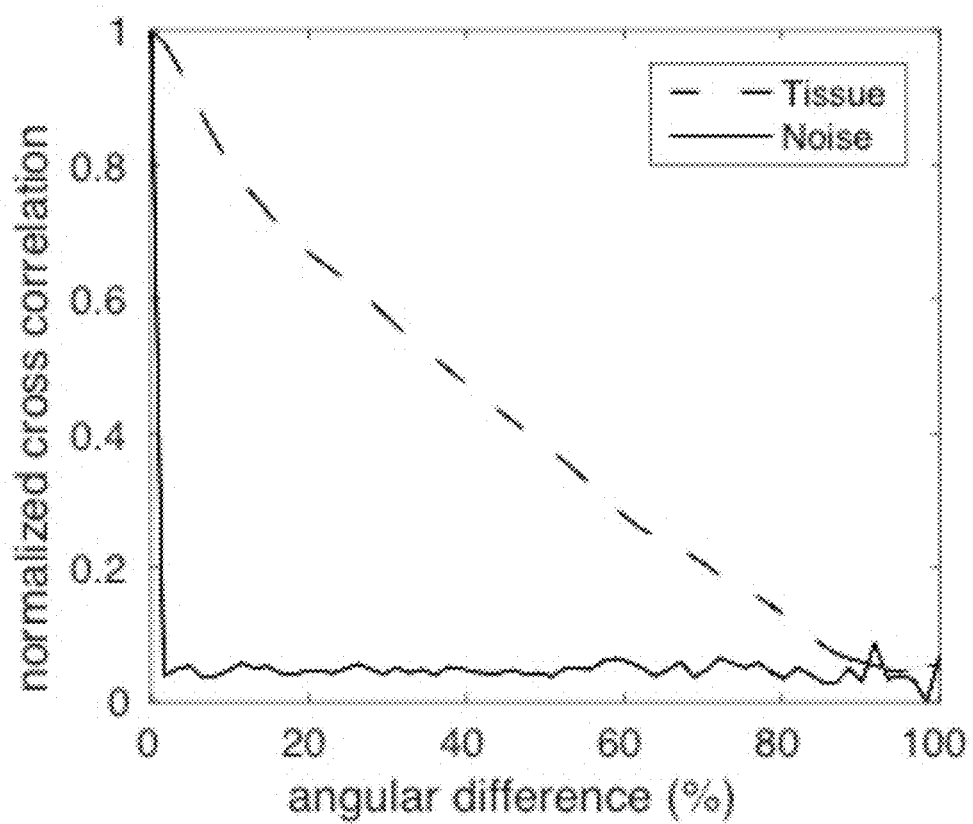
FIG. 4 shows an example of angular coherence of tissue vs. noise.

FIG. 4 shows an example of the normalized correlation function as a function of the differences of the angles of plane waves. The angular difference is represented as a percentage of the maximum angle. The normalized cross correlation function from tissue signal (dashed) and electronic noise (solid) have significant differences. The function calculated from electronic noise decays faster. This difference can be utilized to selectively suppress noise.

Figure 5:
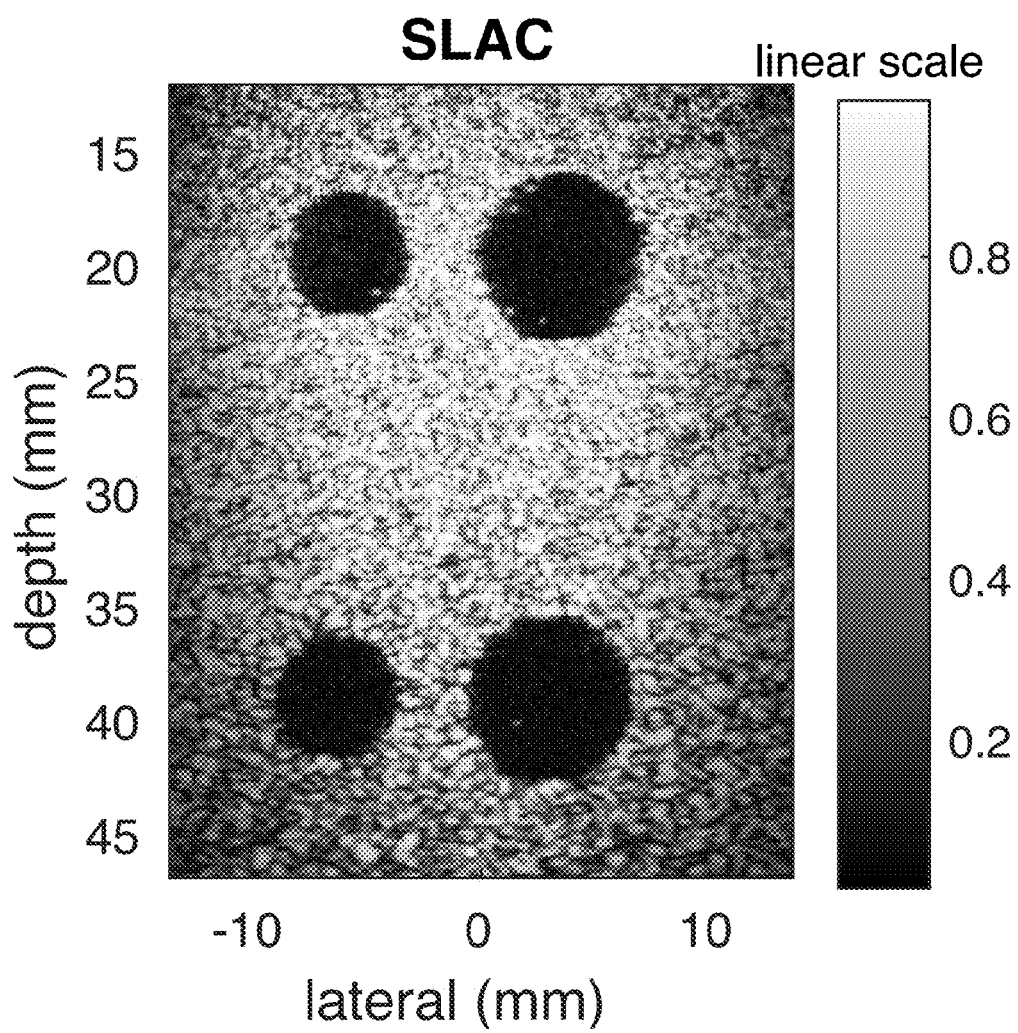
FIG. 5 is a brightness mode angular coherence acoustic image.

FIG. 5 is a brightness-mode image produced with the short-lag angular coherence imaging as described above.

Figure 6A:
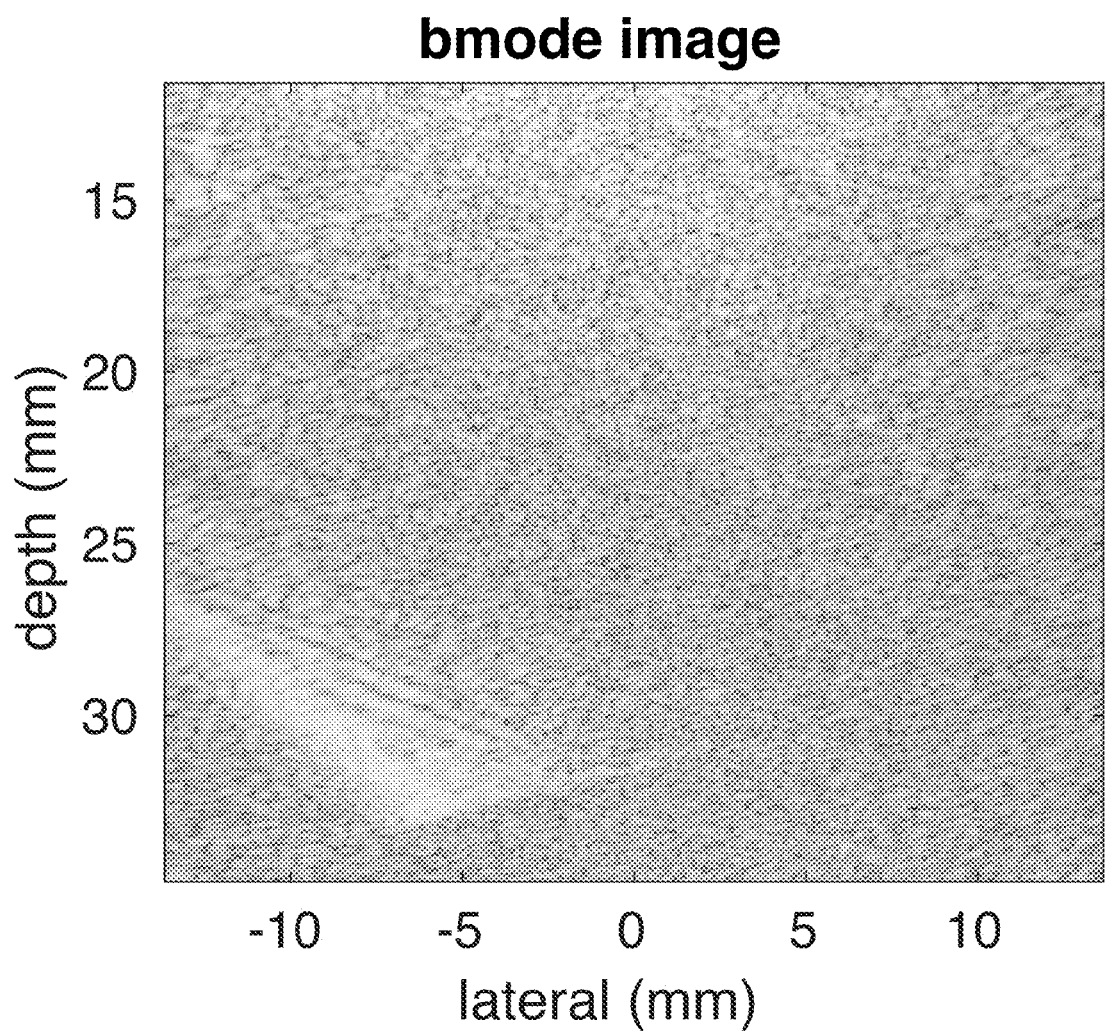
FIG. 6A is an acoustic brightness mode image of a flow phantom.
Figure 6B:
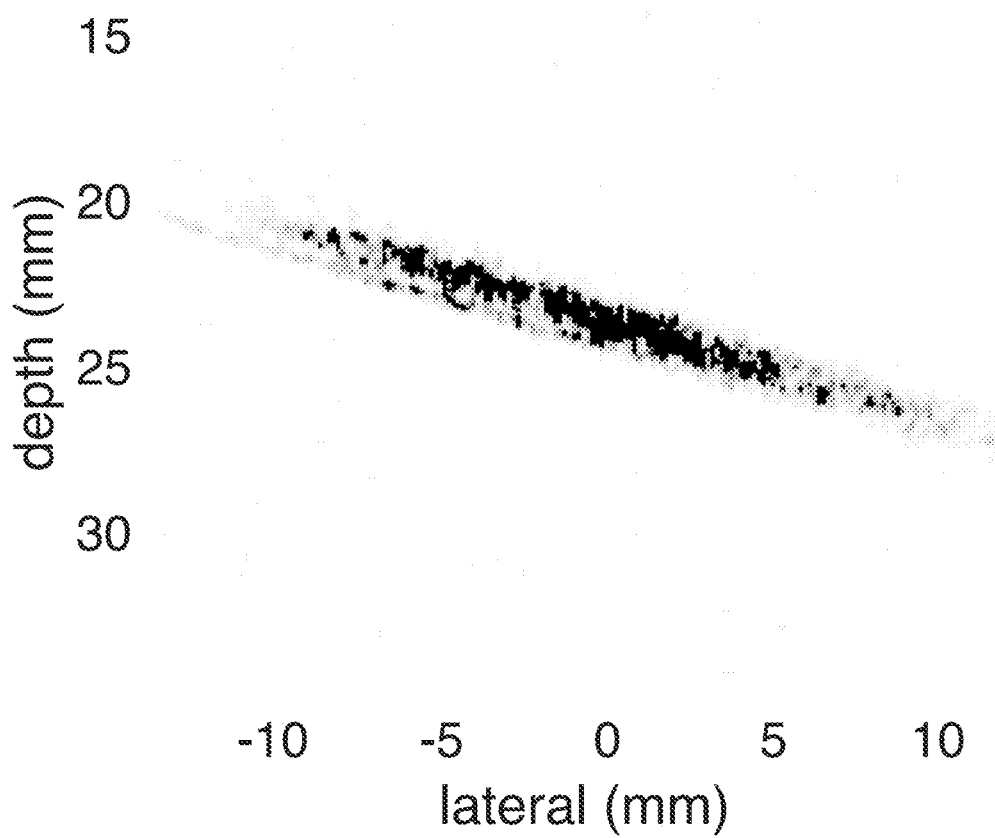
FIG. 6B is an angular coherence acoustic flow image of the flow phantom of FIG. 6A.

FIG. 6A is a brightness-mode image of a flow phantom. FIG. 6B is a flow image (with inverted gray scale) of the flow phantom obtained via short-lag angular coherence imaging. The flow in the phantom is clearly visible in this image.

Mathematical Development

To better appreciate the present invention, the following exemplary mathematical development is provided. The method can be regarded as including 4 major steps.

1. Tissue insonification with a synthetic transmit focusing technique, such as virtual source and plane wave synthetic aperture. (FIG. 2A) In the following example, the method is described using the plane wave synthetic aperture technique, however any synthetic aperture technique can be utilized. First, an ultrasound plane wave is transmitted into the tissue using an ultrasound transducer array.

Figure 2A:
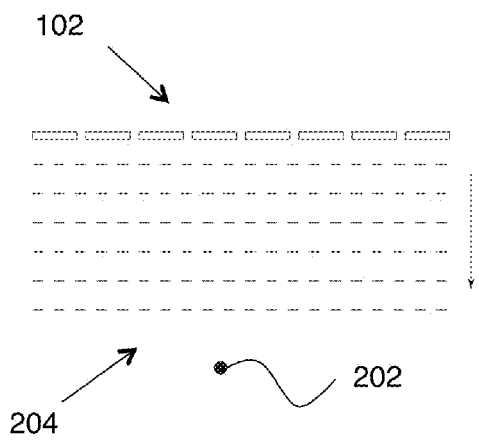
FIGS. 2A-D schematically show examples of incident and scattered acoustic radiation.
Figure 2B:
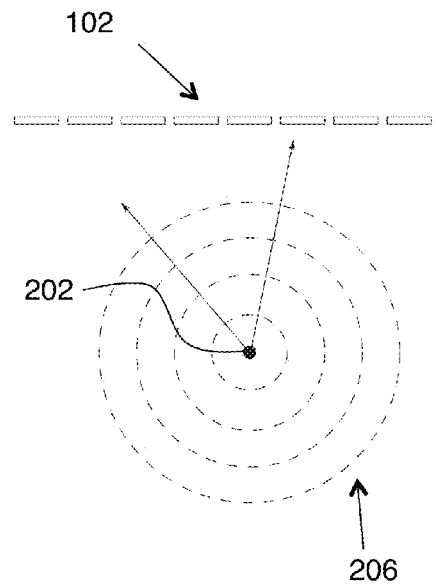

2. Next, the transmitted wave is backscattered by the tissue (FIG. 2B). The backscattered waves from the tissue are received by the transducer array and converted to electronic signals by the ultrasound transducer. The electronic signals from the transducer elements are then delay-and-sum beamformed (i.e. shifted by delays to dynamically focus the received signals and the summed together) using a parallel beamforming technique. That is, the same channel signals are used to dynamically focus the received electronic signals at every point in the desired image domain. This results in a "radiofrequency image" described by f(x,y), where f is the radiofrequency image, and x and y are the lateral and depth coordinates, respectively (or similarly, f(r,θ), with r being the depth or range and theta being an angle).

Figure 2C:
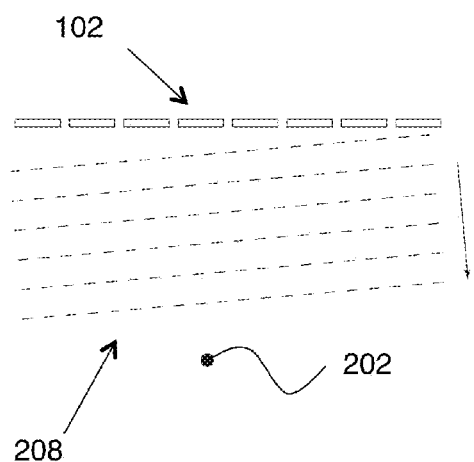
Figure 2D:
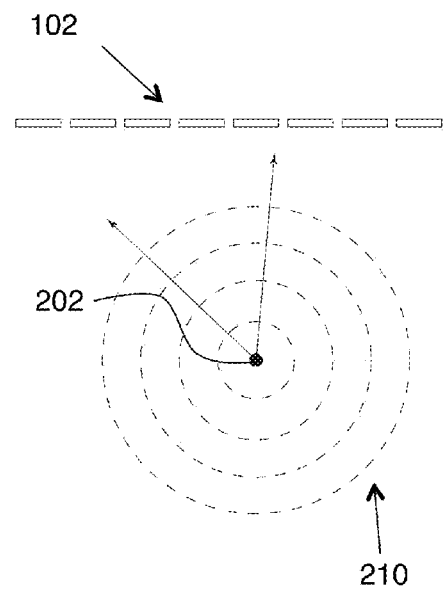

3. The process described in 1 and 2 is repeated with plane waves at M different angles into the tissue (FIGS. 2C-D). This results in M "radiofrequency images" of the same image domain, where the dynamic receive foci in each of the M images are identical (i.e. $f(x,y,\alpha_i)$, where i=1, 2, . . . , M). The number and range of angles can be adjusted to change the focusing quality, however the receive focal locations are identical in each image. Typically, 17 angles covering −8 to 8 degrees would be sufficient to produce a high quality image. Similarly, for virtual source synthetic focusing, a set of 17 "transmits" from virtual sources across the "virtual aperture" is sufficient to produce a high quality image.

4. For the same point in each of the images produced from different transmit angles $\alpha$, the normalized coherence (i.e. a function that computes the similarity of the signals) of every pair of signals received at different plane wave angles are computed as a function of the difference between angles (i.e. the spatial coherence is computed across the angles of $f(x,y,\alpha_1)$).

$$R(x, y, z, \Delta\alpha) = \frac{f(x, y, z, \alpha_1) \cdot f(x, y, z, \alpha_2)}{|f(x, y, z, \alpha_1)| \cdot |f(x, y, z, \alpha_2)|}, \quad (1)$$

in which, $\Delta\alpha = \alpha_1 - \alpha_2 \cdot R(x,y,z,\Delta\alpha)$ is then averaged across the angles $\alpha$ to produced an averaged coherence function $\overline{R}(x,y,z,\Delta\alpha)$.

For the computation of normalized coherence, various techniques can be used to produce similar results. First of all, instead of RF data, the complex IQ (in-phase and quadrature) data can be used as an alternative. Using IQ data, the computation can be represented as $$\overline{R}(x, y, z, \Delta\alpha) = \text{mean}\left(\frac{IQ(x, y, z, \alpha_1) \cdot IQ^*(x, y, z, \alpha_2)}{|IQ(x, y, z, \alpha_1)| \cdot |IQ(x, y, z, \alpha_2)|}\right), \quad (2)$$

where $IQ(x,y,z,\alpha)$ represent the complex IQ signal at location $(x,y,z)$ with transmit angle $\alpha$; $IQ^*(x,y,z,\alpha)$ represent the complex conjugate of $IQ(x,y,z,\alpha)$; and $\|\ \|$ represent the $l_2$ norm of the IQ signal.

In implementation with discrete-time signals, various techniques can be used. For example, $$\overline{R}(x, y, z, \Delta\alpha) = \frac{\sum_{\alpha_1=-\alpha_0}^{\alpha_0} IQ(x, y, z, \alpha_1) \cdot IQ^*(x, y, z, \alpha_1 + \Delta\alpha)}{\sum_{\alpha_1=-\alpha_0}^{\alpha_0} |IQ(x, y, z, \alpha_1)||IQ^*(x, y, z, \alpha_1 + \Delta\alpha)|}, \quad (3)$$

in which, the angular range is from $-\alpha_0$ to $\alpha_0$. The IQ signal $IQ(x,y,z,\alpha)$ can be replaced with RF signal $f(x,y,z,\alpha)$ according to the previous description.

Alternatively, the average can be calculated as $$\overline{R}(x, y, z, \Delta\alpha) = \frac{1}{N}\sum_{\alpha_1=-\alpha_0}^{\alpha_0} \frac{IQ(x, y, z, \alpha_1) \cdot IQ^*(x, y, z, \alpha_1 + \Delta\alpha)}{|IQ(x, y, z, \alpha_1)||IQ^*(x, y, z, \alpha_1 + \Delta\alpha)|}, \quad (4)$$

in which, N represent the number of angles $\alpha_1$ between the range $-\alpha_0$ and $\alpha_0$ used in the computation. Additionally, a spatial kernel can be used in any of the implementations above. For example, using an axial kernel in z dimension in the implementation follows $$\overline{R}(x, y, z) = \frac{\sum_{\alpha_1=-\alpha_0}^{\alpha_0}\sum_{z_i=z-z_0}^{z+z_0} Q(x, y, z_i, \alpha_1) \cdot IQ^*(x, y, z_i, \alpha_1 + \Delta\alpha)}{\sum_{\alpha_1=-\alpha_0}^{\alpha_0} \text{sqrt}\left(\sum_{z_i=z-z_0}^{z+z_0} |IQ(x, y, z_i, \alpha_1)|^2 \sum_{z_i=z-z_0}^{z+z_0} |IQ^*(x, y, z_i, \alpha_1 + \Delta\alpha)|^2\right)}, \quad (5)$$

in which the axial kernel length is $2z_0$, and $z_i$ is the summation variable. The function sqrt( ) represent the square root function. Another example is $$\overline{R}(x, y, z, \Delta\alpha) = \frac{1}{N}\sum_{\alpha_1=-\alpha_0}^{\alpha_0} \frac{\sum_{z_i=z-z_0}^{z+z_0} IQ(x, y, z_i, \alpha_1) \cdot IQ^*(x, y, z_i, \alpha_1 + \Delta\alpha)}{\text{sqrt}\left(\sum_{z_i=z-z_0}^{z+z_0} |IQ(x, y, z_i, \alpha_1)|^2 \sum_{z_i=z-z_0}^{z+z_0} |IQ^*(x, y, z_i, \alpha_1 + \Delta\alpha)|^2\right)}. \quad (6)$$

Similar kernels in x and y dimensions can be used as well.

The pixel value of the resulting image point, $g(x,y)$, is then calculated by integrating or summing the normalized spatial coherence function between 0 and 30% of the maximums difference between the angles.

$$g(x,y) = \int_0^\rho \overline{R}(x,y,\Delta\alpha) d\Delta\alpha, \quad (7)$$

in which, $\rho \approx A \cdot \Delta\alpha_{max}$, where A is a fraction, usually between 0.01 and 0.3 and represents the fraction of the aperture width or fraction of the total angle encompassing all transmits.

The process is carried out for each pixel (x, y), and a B-mode image can be produced (FIG. 6A). Because the spatial coherence curve produced from the tissue signal and the coherence functions results from incoherent noise, such as electronic noise or reverberation, are different (FIG. 4), this method can selectively suppress electronic noise and improve image quality.

The normalized angular coherence function for plane-wave transmits $A_{PWT}$ can be expressed as $$A_{PWT}(\Delta p, \Delta q) = \frac{C_{rx}(k\Delta p, k\Delta q)}{C_{rx}(0, 0)} \quad (8)$$

where $\Delta p = p_1 - p_2$, $\Delta q = q_1 - q_2$, $C_{rx}$ is the autocorrelation of the receive aperture function, k is the wave number and p and q are normalized spatial frequencies (i.e., p and q are effectively angles).

The physical implication of Eq. (8) is that the cross-correlation function of the backscattered signals from plane-wave transmits at different angles and a spatially incoherent homogeneous medium is proportional to the normalized autocorrelation of the receive aperture function. This can be considered as an extension to the van Cittert Zernike theorem.

The transmit angular spacing ($k\Delta p$, $k\Delta q$) in Eq. 8 can be expressed as fractions of the maximum angle sampled by the receive aperture $(\eta_p, \eta_q) = (k\Delta_p/kp_{max}, k\Delta q/q_{max})$ as $$A_{PWT}(\eta_p, \eta_q) = \frac{C_{rx}(\eta_p, \eta_q)}{C_{rx}(0, 0)} \quad (9)$$

in which, $0 \leq \eta_p, \eta_q \leq 1$. If the transmit angular spacing is greater than the maximum angle sampled by the receive aperture (i.e., $\eta_p$ or $\eta_q > 1$), $A_{PWT}(\eta_p, \eta_q) = 0$.

In cases where flow imaging is performed, transmission from the 17 angles or virtual elements are repeated multiple times, and the images g(x,y,i) from the acquisitions are summed using a power estimator, $$P(x,y) = \sum_{i=1}^{N} g^2(x,y,i), \quad (10)$$

in which, g(x,y,i) is the angular coherence image produced from the $i_{th}$ acquisition, and N is the number of acquisitions. P(x,y) is the flow image (FIG. 6B).

In addition, both the B-mode image g(x,y) and the flow image P(x,y) can be computed using the "recursive" method. That is, the signals from the same angle or virtual element, but previous cycle, are updated with the values from the new transmission, and P(x,y) are recalculated, thus improving frame rate and continuity of the image.

The invention claimed is:

1. A method for acoustic imaging, the method comprising:
   providing an acoustic imaging system including an acoustic transducer array and a processor;
   emitting collimated acoustic radiation from the acoustic transducer array at a target at three or more distinct incidence angles;
   receiving scattered acoustic radiation from the target with the acoustic transducer array;
   determining acoustic images of the target from the scattered acoustic radiation corresponding to each of the three or more incidence angles;
   computing an angular coherence image with the processor by
   i) averaging the acoustic images vs. angle to estimate an angular coherence function at each spatial point of the acoustic images;
   ii) integrating the angular coherence function over a predetermined angular range to provide the angular coherence image;
   providing the angular coherence image as an output.

2. The method of claim 1, wherein the predetermined angular range is less than or equal to 30% of a total angular range of the three or more distinct incidence angles.

3. The method of claim 1, wherein the acoustic images are provided as complex-valued functions of two spatial variables or as real-valued functions of two spatial variables.

4. The method of claim 3, wherein the complex-valued functions are represented as having real and imaginary components in the averaging the acoustic images vs. angle.

5. The method of claim 3, wherein the complex-valued functions are represented as having in-phase and quadrature components in the averaging the acoustic images vs. angle.

6. The method of claim 3, wherein the real-valued functions represent radio-frequency ultrasound signal intensity in the averaging the acoustic images vs. angle.

7. The method of claim 1, wherein the averaging the acoustic images vs. angle further comprises spatial averaging over a predetermined spatial range.

8. The method of claim 7, wherein the acoustic imaging system provides an axial resolution and wherein the spatial averaging is done over an axial range substantially equal to the axial resolution.

9. The method of claim 7, wherein the acoustic imaging system provides a lateral resolution and wherein the spatial averaging is done over a lateral range substantially equal to the lateral resolution.

10. The method of claim 1, wherein the acoustic images are 2-D brightness mode images.

11. The method of claim 1, wherein the three or more distinct incidence angles are seven or more distinct incidence angles.

12. A method of flow acoustic imaging comprising:
    performing the method of claim 1 for three or more acquisitions, wherein the acoustic images are flow acoustic images that are filtered to suppress signals from stationary parts of the target, and wherein the acquisitions are separated by a predetermined time delay;
    providing an output flow image by summing squares of the angular coherence image for each acquisition.

* * * * *